(12) United States Patent
Matz et al.

(10) Patent No.: US 6,691,715 B2
(45) Date of Patent: Feb. 17, 2004

(54) WATER SOLUBLE POLYMER COMPOSITION AND METHOD OF USE

(75) Inventors: Gary F. Matz, Carnegie, PA (US); Randy J. Loeffler, Carnegie, PA (US); Shih-Ruey T. Chen, Pittsburg, PA (US); Allan L. Melby, Cranberry Township, PA (US); Nicholas F. Vozza, Burgettstown, PA (US)

(73) Assignee: Calgon Corporation, Naperville, IL (US)

( * ) Notice: Subject to any disclaimer, the term of this patent is extended or adjusted under 35 U.S.C. 154(b) by 6 days.

(21) Appl. No.: 10/243,285

(22) Filed: Sep. 13, 2002

(65) Prior Publication Data

US 2003/0022987 A1 Jan. 30, 2003

Related U.S. Application Data

(62) Division of application No. 09/617,568, filed on Jul. 17, 2000, now abandoned.
(60) Provisional application No. 60/144,149, filed on Jul. 16, 1999.

(51) Int. Cl.$^7$ .............................. A61K 7/04; A61K 7/06; A61K 7/48; C08F 220/06; C08F 220/56
(52) U.S. Cl. ................ 132/202; 526/303.1; 526/307.2; 526/307.3; 526/307.4
(58) Field of Search ...................... 132/202; 526/303.1, 526/307.2, 307.3, 307.4

(56) References Cited

U.S. PATENT DOCUMENTS

| | | | |
|---|---|---|---|
| 4,065,422 A | 12/1977 | Lundmark et al. | |
| 4,077,930 A | 3/1978 | Lim et al. | |
| 4,128,631 A | 12/1978 | Lundmark et al. | |
| 4,455,240 A | 6/1984 | Costello | |
| 4,652,623 A | 3/1987 | Chen et al. | |
| 4,726,906 A | 2/1988 | Chen et al. | |
| 4,772,462 A | 9/1988 | Boothe et al. | |
| 4,842,849 A | 6/1989 | Grollier et al. | |
| 5,032,295 A | 7/1991 | Matz et al. | |
| 5,296,218 A | 3/1994 | Chen et al. | |
| 5,405,544 A | 4/1995 | Esche et al. | |
| 5,480,921 A | 1/1996 | Hunter et al. | |
| 5,609,862 A | 3/1997 | Chen et al. | |
| 5,653,886 A | 8/1997 | Kerr et al. | |
| 5,849,862 A | * 12/1998 | Davies et al. | ........... 528/502 E |
| 5,879,670 A | 3/1999 | Melby et al. | |

FOREIGN PATENT DOCUMENTS

| | | | |
|---|---|---|---|
| EP | 161763 A | * 11/1985 | ........... C08F/02/32 |

* cited by examiner

*Primary Examiner*—Kelechi C. Egwim
(74) *Attorney, Agent, or Firm*—Michael B. Martin; Thomas M. Breininger

(57) ABSTRACT

Novel water soluble polymers in solution or water-in-oil emulsion form are disclosed containing quaternary ammonium monomers; and optionally (meth)acrylic acid or 2-(meth)acrylamido-2-methylpropane sulfonic acid; methylene bis-acrylamide and the like; and a $C_1$–$C_3$ alkyl (meth)acrylate acrylamide or methacrylamide and the use thereof in hair, skin and nail conditioning; papermaking; and subterranean well drilling and well cementing operations.

5 Claims, No Drawings

WATER SOLUBLE POLYMER COMPOSITION AND METHOD OF USE

CROSS REFERENCE TO RELATED APPLICATIONS

This is a divisional of Ser. No. 09/617,568, filed Jul. 17, 2000 now abandoned which claims the benefit of Provisional application No. 60/144,149 filed Jul. 16, 1999.

FIELD OF THE INVENTION

The present invention relates to novel water soluble ampholyte polymers, polymer compositions and methods for using such polymers in applications wherein polymer deposition and substantivity is important. In general terms, the polymers and polymer compositions of the present invention are believed to be useful in the treatment of substrates or used in combination with substrates such as those that are composed primarily of keratin, cellulose, minerals, pigments, clays and cement.

BACKGROUND OF THE INVENTION

The interaction of polyelectrolyte with substrates that carry a charge is at the heart of many industrial processes. The basic science that explains the function of coagulants and flocculants can be applied to many end use applications, such as paper manufacturing, conditioning hair and skin, dispersion and suspension stabilization, as well as fluid loss control in oil field cementing and drilling operations.

For example, the surface properties of keratin are of interest in cosmetic science, and there has been a long-standing desire to discover ingredients, which will beneficially affect the topical and bulk condition of keratinous substrates, such as hair. The term "keratin" used herein refers to human or animal hair, skin and/or nails. For example, such ingredients must have adequate adherent properties, so that they are not only adsorbed initially, but are also retained on exposure to water. This property is referred to as "substantivity", i.e., the ability of a material to be adsorbed onto keratin and to resist removal by water rinse-off.

Hair is composed of keratin, a sulfur-containing fibrous protein. The isoelectric point of keratin, and more specifically of hair, is generally in the pH range of 3.2–4.0. Therefore, at the pH of a typical shampoo, hair carries a net negative charge. Consequently, cationic polymers have long been used as conditioners in shampoo formulations, or as a separate treatment, in order to improve the wet and dry combability of the hair. The substantivity of the cationic polymers for negatively charged hair along with film formation facilitates detangling during wet hair combing and a reduction in static flyaway during dry hair combing. Cationic polymers generally also impart softness and suppleness to hair.

When cationic polymers are added to shampoos (or to skin care products such as cleaning compositions) containing anionic surfactants, formation of highly surface active association complexes generally takes place, which imparts improved foam stability to the shampoo. Maximum surface activity and foam stability, or lather, are achieved at near stoichiometric ratios of anionic surfactant: cationic polymer, where the complex is least water soluble. Generally, cationic conditioners exhibit some incompatibility at these ratios. Compatibility gives a commercially more desirable clear formulation, while incompatibility leads to a haze or precipitation, which is aesthetically less desirable in some formulations.

In many situations, there is a trade off between high cationic charge content, which leads to good substantivity and the ability to formulate clear stable formulations. The need for a highly substantive water soluble polymer that can be formulated into clear products is needed in the personal care industry.

Polyelectrolytes are also used in the papermaking process. Papermaking, as it is conventionally known, is a process of introducing an aqueous slurry of pulp or wood cellulosic fibers (which have been beaten or refined to achieve a level of fiber hydration and to which a variety of functional additives can be added) onto a screen or similar device in such a manner that the water is removed, thereby forming a sheet of the consolidated fibers, which upon pressing and drying can be processed into dry roll or sheet form. Two well known papermaking operations involve the Fourdrinier machine, the most common, and the cylinder machine. In the Fourdrinier and multicylinder operations, and in other machine operations, as typical in papermaking, the feed or inlet to the machine is an aqueous slurry or water suspension of pulp fibers which is provided from what is called the "wet end" system. In the wet end, the pulp along with other additives are mixed in an aqueous slurry and subject to mechanical and other operations such as beating and refining to improve interfiber bonding and other physical properties of the finished sheet. Additives commonly introduced along with the pulp fibers are pigments such as titanium dioxide, mineral fillers such as clay and calcium carbonate and other materials introduced into paper to achieve such properties as improved brightness, opacity, smoothness, ink receptivity, fire retardant, water resistance, increased bulk, etc. Also useful in papermaking are colloidal inorganic minerals, such as colloidal silica, which are added to what is typically known as a microparticle system to give better sheet formation.

The term "paper, as used herein, includes sheet-like masses and molded products made from natural sources, synthetics such as polyamides, polyesters, rayon and polyacrylic resins as well as from mineral fibers such as asbestos and glass. In addition, paper made from combinations of cellulosic and synthetic materials are applicable herein. Paperboard is also included within the broad term "paper".

There remains a need for an additive that will substantively bind the fibers and other additives while not negatively impacting water removal from the forming sheet.

In an ink jet recording method, recording is generally carried out by jetting fine drops of ink using a variety of mechanisms so as to form images on a recording paper. Therefore, the recording method of ink jet type has advantages in that it is less noisy, can provide full-color prints with ease and enables high-speed printing, compared with the recording method of dot impact type.

For the paper used in such an ink jet recording method, it is usually required to have properties of (1) ensuring high-speed drying of ink, (2) being free from cissing, feathering and overflowing of ink, (3) providing recorded images of high optical density, and (4) causing no rippling trouble upon absorption of ink.

In addition, ink jet printers have had remarkable development in recent years, so that they have come to ensure considerable colorfulness and vividness in the recorded images. Thus, recording media also have been required to be higher grade merchandise. As matters now stand, it is known that higher grade recorded image which can give such a feeling of higher quality as those provided by photography or high grade printed matter can be obtained by choosing a recording medium having a glossy surface.

However, the need for reduction in running cost has also grown in proportion as prices of ink jet printers have declined. Since most of glossy recording media on the market use as their substrates more expensive materials, such as plastic films or laminated papers, they cannot meet the aforesaid need.

In contrast to the recording media on the market in which films or the like are used as substrate, cast-coated paper uses low-priced paper as a substrate and can be prepared in a relatively simple process, so that it has the advantage of a substantially lower cost. Further, as the recording side of cast-coated paper can be rendered glossy, the cast-coated paper is suitable for ink jet recording paper which can give a feeling of high quality and can provide high grade recorded images at a lower price.

High grade ink jet images depend on the formation of "dots" that contrast sharply with the color of the paper. If the ink jet dyes "wick into the paper with the ink vehicle, "fuzzy" dot boundaries result and color intensity is decreased. There remains a need for a material that will substantively bind dye or pigment particles to the surface of ink jet printed paper so that sharply contrasting intense dots are formed.

Another area in which polyelectrolytes provide benefit is in drilling fluids. It is well known that in perforating earthen formations to tap subterranean deposits such as gas or oil, that perforation is accomplished by well drilling tools and a drilling fluid. These rotary drilling systems consist of a drilling bit fitted with appropriate 'teeth', then a set of pipes assembled rigidly together end to end, the diameter of which is smaller than that of the drilling bit. This whole rigid piece of equipment, drill bit and drill pipe string, is driven into rotation from a platform situated above the well being drilled. As the drill bit attacks and goes through the geological strata, the crushed mineral materials must be cleared away from the bottom of the hole to enable the drilling operation to continue. Aqueous clay dispersion drilling fluids are recirculated down through the hollow pipe, across the face of the drill bit, and upward through the hole. The drilling fluid serves to cool and lubricate the drill bit, to raise the drilling cuttings to the surface of the ground, and to seal the sides of the well to prevent loss of water and drilling fluids into the formation through which the drill hole is being bored. After each passage through the well, the mud is passed through a settling tank or trough wherein the sand and drill cuttings are separated, with or without screening. The fluid is then again pumped into the drill pipe by a mud pump.

Some of the most serious problems encountered in producing and maintaining effective clay-based aqueous drilling fluids are caused by the interaction of the mud with the earth formation being drilled. These interactions include contamination of the mud by formation fluids, incorporation into the mud of viscosity producing and inert drilled solids, chemical contamination by drilled solids, or by the infiltration of sea-water and/or fresh water. The conditions of high temperature and pressure inherent with deeper and deeper drilling operations, together with formation interactions, make drilling fluid behavior unreliable and difficult to reproduce.

Characteristics of an ideal drilling fluid would then include the following:
i) To have rheological characteristics as desirable as possible to be able to transport the mineral cuttings set in dispersion.
ii) To allow the separation of cuttings by all known means as soon as the mud flows out of the hole.
iii) To have such required density as to exert sufficient pressure on the drilled geological formations.
iv) To retain its fundamental rheological qualities as it is submitted, in very deep drilling, to higher and higher temperatures.

There remains a need for a material, which will provide these functions while not being degraded by the mechanical action of drilling.

Polyelectrolytes are also used in oil field cementing operations. Hydraulic cement compositions are used for carrying out various operations in oil, gas and water wells including, but not limited to construction and completion operations such as primary cementing and remedial operations such as squeeze cementing. Primary cementing involves the placement of a hydraulic cement composition into the annular space between the walls of a well bore and the exterior of a pipe such as casing disposed therein. The cement composition is pumped into the annular space and allowed to set into an annular cement sheath therein whereby the pipe is bonded to the walls of the well bore by the set cement.

As used herein, the term "cement" refers to portland cement, concrete and other mixtures of calcium oxide and sand.

Squeeze cementing techniques usually involve the undesirable movement of oil, gas or water through small holes or cracks in pipe disposed in the well bore; holes, cracks, voids or channels in the annular cement sheath between the pipe and the well bore; annular spaces between the cement sheath and the pipe or the walls of the well bore and permeable zones or fractures in subterranean formations. Such holes, cracks, etc. are plugged by squeezing hydraulic cement compositions therein which harden and form impermeable plugs.

In performing cementing operations in such wells, the cement compositions are often subjected to high temperatures, particularly when the cementing is carried out in deep subterranean zones. The high temperatures can cause premature setting of the cement compositions, i.e., the compositions can not be pumped for long enough times before setting to place them in the zones to be cemented. This requires the use of set retarding additives in the cement compositions which extend the setting times of the compositions so that adequate pumping time is provided in which to place or displace the compositions into desired subterranean zones.

There remains a need for a polymer, which will not degrade under the temperatures, pressures and mechanical action of oil field cementing operations.

In all of the applications outlined above, polymers have been used to improve the properties of the substrate or minimize adverse consequences. For example if the substrate is hair, polymers have been used to improve the detangling and combing of hair after shampooing. During paper manufacture, polymers are used to provide faster dewatering of the sheet, which leads to faster, more economical machine utilization. Polymers are also added during paper manufacture to improve the strength, or resistance to tearing, of the resulting sheet. Polymers are also added to paper coatings to improve the gloss of the sheet and to provide a surface that results in fast drying well defined dots from the ink jet printing process. Polymers are added to drilling fluids and cementing compositions to aid in performance and minimize water loss to the surrounding rock formation. In all of these applications, the polymer must be substantive to the substrate, meaning that it will adhere or adsorb onto the substrate surface and not be easily removed.

Although many polymers are used in the aforementioned applications, there still remains a shortcoming in that they can be removed from the substrate due to physical action.

U.S. Pat. No. 4,842,849 discloses compositions suitable for treating keratin comprising at least one cationic polymer including poly(dimethyldiallylammonium chloride), and at least one anionic polymer containing vinylsulfonic groups, optionally copolymerized with acrylamide. The cationic polymer may be an amphoteric polymer as defined.

EP 0 080 976 discloses aqueous hair-cosmetic compositions containing a surface active polymeric acrylic-based quaternary ammonium salt, a monomeric or oligomeric ammonium salt, and a surface active nonionic, anionic or zwitterionic component.

U.S. Pat. Nos. 4,128,631 and 4,065,422 disclose a method of imparting lubricity to keratinous substrates such as skin or hair by contacting said substrates with a salt of 2-acrylamido-2-methylpropane sulfonic acid (AMPSA) having a molecular weight of from 1–5 million.

U.S. Pat. No. 4,772,462 discloses hair products containing a copolymer of dimethyl diallyl ammonium chloride and acrylic acid. These polymers are limited in that they rely solely on ionic interactions to be substantive to substrates.

U.S. Pat. Nos. 5,296,218; 5,609,862; and 5,879,670 disclose ampholyte polymers including terpolymers providing superior conditioning properties in shampoos and other hair care products. These polymers also rely primarily on ionic interactions for substantivity, however, the ionic charge is pH dependent which limits utility.

U.S. Pat. No. 4,077,930 discloses ampholyte polymers in a water in oil emulsion from that are useful as drainage and retention aids during the manufacture of paper. These polymers have limited utility as their only means of achieving substantivity is through ionic mechanisms.

U.S. Pat. Nos. 4,455,240; 4,652,623; 4,726,906; and 5,032,295 disclose ampholyte polymers for use as filtration control aids in drilling muds. These polymers rely only on ionic interactions to achieve substantivity, however, the charge in the polymers changes with pH which limits utility.

SUMMARY OF THE INVENTION

The composition comprises a water soluble ampholyte polymer containing monomer moieties of: (a) at least one monomer selected from the group consisting of acrylamidopropyltrimethyl ammonium halide, methacrylamidopropyltrimethyl ammonium halide, methyloyloxyethyl trimethyl ammonium halide, methyloyloxyethel trimethyl ammonium methylsulfates, acryloyloxyethyl trimethylammonium halide, and dimethyl diallyl ammonium halide; b) 0 to 80 mol % of a monomer selected from the group consisting of acrylic acid, methacrylic acid, 2-acrylamido-2-methylpropane sulfonic acid and 2-methacrylamido-2-methylpropane sulfonic acid; c) at least one monomer selected from the group consisting of N,N'-methylenebisacrylamide (MBA), triallyl methyl ammonium chloride (TAMAC), allyl methacrylate (AM), n-methylol acrylamide (nMA), polyethylene glycol dimethacrylate (PEGDMA), ethylene glycol dimethacrylate (EGDMA), diethylene glycol dimethacrylate (DEGDMA), 1,6-hexanediol dimethacrylate (HDMA), and allyl sucrose (AS); and (d) 0 to about 70 mol % of a nonionic monomer selected from the group consisting of $C_1$–$C_3$ alkyl acrylate, $C_1$–$C_3$ alkyl methacrylate, acrylamide, n-alkylacrylamide, methacrylamide, n-alkylmethacrylamide, and diacetone acrylamide; wherein the weight average molecular weight of said polymer, as determined by viscometry, is at least about 10,000.

The composition according to the present invention alternatively comprises a water-in-oil emulsion polymer containing: 10 to 60% by weight of a hydrophobic oil phase comprised of one or more oils selected from the list of mineral oil, synthetic oil, modified oil or vegetable oil; 0.5 to 10% by weight of a surfactant system comprised of one or more surfactants selected from the list of oil-soluble alkanolamides, polyoxyethylene derivatives of sorbitan esters, sorbitan monooleate, sorbitan monostearate, $C_6$–$C_{22}$ linear or branched alkyl ethoxylate with 1 to 30 oxyethylene units, $C_6$–$C_{22}$ linear or branched alkyl propoxylate with 1 to 30 oxypropylene units, $C_6$–$C_{22}$ linear or branched alkyl ethoxylate/propoxylate with 1 to 30 combined oxyethylene and propoxylate units, hexadecyl sodium pthalate, cetyl or stearyl sodium pthalate, ethylene oxide condensates of fatty acid amides; and 5 to 90% by weight of a polymerizable aqueous phase comprising water and a polymer, the monomers in the polymer comprising: (a) 1 to about 100 mol % acrylamidopropyl-trimethyl ammonium chloride (APTAC), methacrylamidopropyltrimethyl ammonium chloride (MAPTAC), methyloyloxyethyl trimethyl ammonium chloride (METAC) methyloyloxyethyl trimethyl ammonium methylsulfate (METAMS), acryloyloxyethyl trimethyl ammonium chloride (AETAC) and/or dimethyl diallyl ammonium chloride (DMDAAC); (b) 0 to about 80 mol % acrylic acid (AA), methacrylic acid (MAA), 2-acrylamido-2-methylpropane sulfonic acid (AMPSA) and/or 2-methacrylamido-2-methylpropane sulfonic acid (MAMPSA); (c) 0 to about 1 mol % N,N'-methylenebisacrylamide (MBA), triallyl methyl ammonium chloride (TAMAC), allyl methacrylate (AM), n-methylol acrylamide (nMA), polyethylene glycol dimethacrylate (PEGDMA), ethylene glycol dimethacrylate (EGDMA), diethylene glycol dimethacrylate (DEGDMA), 1,6-hexanediol dimethacrylate (HDMA), and allyl sucrose (AS) and (d) 0 to about 70 mol percent, of a nonionic monomer selected from $C_1$–$C_3$ alkyl acrylate, $C_1$–$C_3$ alkyl methacrylate, acrylamide, n-alkyl acrylamide, methacrylamide, n-alkylmethacrylamide and/or diacetone acrylamide; wherein the molecular weight of the resulting polymer is greater than 10,000.

DETAILED DESCRIPTION OF THE INVENTION

The water soluble ampholyte polymers of the present invention and compositions containing such polymers are novel and unexpected because of their unique structure and improved substantivity.

The instant invention is directed to novel water soluble ampholyte polymers and polymer compositions and to the use of the same in the treatment of various substrates such as keratin, cellulose, paper, pigments, minerals, clays or cements.

As used herein, keratin substrates include, but are not limited to, animal and human hair, skin and nails. Cellulosic substrates include, but are not limited to paper, cardboard and films. Minerals include, but are not limited to calcium carbonate, aluminum oxide, calcium sulfate and talc. Pigments include, but are not limited to titanium dioxide and iron oxide. Clays include, but are not limited to kaolinite, bentonite and anorthite. Cement includes, but is not limited to portland cement, concrete and other mixtures of calcium oxide and sand.

A particular embodiment of the instant invention is directed to a branched or crosslinked ampholyte polymer prepared from or comprising monomer moieties of: (a) 1 to about 99 (99.999) mol %, of at least one monomer selected from the group consisting of acrylamidopropyl-trimethyl ammonium chloride (APTAC), methacrylamidopropyltrimethyl ammonium chloride (MAPTAC), methyloyloxyethyl trimethyl ammonium chloride (METAC) methyloyloxyethyl trimethyl ammonium methylsulfate (METAMS), acryloyloxyethyl trimethyl ammonium chloride (AETAC) and/or dimethyl diallyl ammonium chloride (DMDAAC); (b) 0 to about 80 mol % of a monomer selected from the group consisting of acrylic acid (AA), methacrylic acid (MAA), 2-acrylamido-2-methylpropane sulfonic acid (AMPSA) and/or 2-methacrylamido-2-methylpropane sulfonic acid (MAMPSA); (c) 0.0001 to about 1 mol %, of at least one monomer selected from the group consisting of N,N'-methylenebisacrylamide (MBA), triallyl methyl ammonium chloride (TAMAC), allyl methacrylate (AM), n-methylol acrylamide (nMA), polyethylene glycol dimethacrylate (PEGDMA), ethylene glycol dimethacrylate (EGDMA), diethylene glycol dimethacrylate (DEGDMA), 1,6-hexanediol dimethacrylate (HDMA), and allyl sucrose (AS); and (d) 0 to about 70 mol percent, of a nonionic monomer selected from the group consisting of $C_1$–$C_3$ alkyl acrylate, $C_1$–$C_3$ alkyl methacrylate, acrylamide, n-alkyl acrylamide, methacrylamide, n-alkylmethacrylamide and/or diacetone acrylamide. Preferably, the mol ratio of a):b) in said branched ampholytic polymer ranges from about 20:80 to about 95:5, more preferably from about 25:75 to about 75:25. Further, the weight average molecular weight of said polymer, as determined by viscometry, is at least about 10,000, preferably from about 50,000 to about 10,000,000, more preferably from about 100,000 to about 8,000,000. Alternatively, gel permeation chromatography (GPC) with light scattering detection can be used.

Preferably, the mol ratio of a):b) ranges from 25:75 to about 75:25, the preferred polymers contain 0.0001 to 0.1 mol % of branching or crosslinking agent c), and the preferred polymers contain d), the nonionic monomers in an amount of at least about 1 up to about 50 mol % of the above-defined $C_1$–$C_3$ acrylate or $C_1$–$C_3$ methacrylate esters, acrylamides or methacrylamides. More preferably, the instant polymers contain about 5 to about 35 mol % of the $C_1$–$C_3$ alkyl acrylate or $C_1$–$C_3$ alkyl methacrylate esters, acrylamides or methacrylamides. In the most preferred case, the nonionic monomer (d) is methyl acrylate, methyl methacrylate, acrylamide or methacrylamide.

The instant invention in this embodiment is also directed to a water soluble branched or crosslinked ampholyte polymer comprising:

a) about 20 to about 95 mol % APTAC, MAPTAC, METAC, METAMS, AETAC or DMDAAC, preferably MAPTAC or DMDAAC;
b) about 5 to about 80 mol % acrylic acid, methacrylic acid, AMPSA or MAMPSA, preferably acrylic acid;
c) about 0.0001 to about 0.1 mol % MBA, TAMAC. AM, nMA, PEGDMA, EGDMA, DEGDMA, HDMA or AS, preferably MBA, TAMAC or AS; and
d) 0.1 to about 20 mol %, preferably 1 to about 50 mol %, of a $C_1$–$C_3$ alkyl acrylate, $C_1$–$C_3$ alkyl methacrylate, acrylamide, n-alkyl acrylamide, methacrylamide, n-alkylmethacrylamide and/or diacetone acrylamide, preferably methyl acrylate, methyl methacrylate, acrylamide and methacrylamide and most methyl acrylate and acrylamide, wherein the molecular weight of said polymers is at least about 10,000.

Preferably, the instant invention in this embodiment is directed to a water soluble branched or crosslinked ampholyte polymer comprising:

a) about 25 to about 75 mol % DMDAAC, APTAC or MAPTAC;
b) about 25 to 75 mol % acrylic acid or methacrylic acid;
c) about 0.0001 to 0.1 mol % MBA, TAMAC or AS; and
d) about 1 to about 35 mol % of a $C_1$–$C_3$ alkyl acrylate, $C_1$–$C_3$ alkyl methacrylate, acrylamide, n-alkyl acrylamide, methacrylamide, n-alkylmethacrylamide and/or diacetone, wherein the molecular weight of said polymer is at least about 10,000.

In an alternative embodiment of the present invention, the polymer can be prepared by using a water-in-oil polymerization process, thus preparing the polymer in an emulsified form. If this type of processing is used, the use of the branching or crosslinked agent is optional because of the resulting high molecular weight of the polymer. Generally, the weight average molecular weight of these polymers is well over 100,000, usually over 1,000,000. Water-in-oil emulsions are comprised of three components, including: (1) an aqueous phase; (2) a hydrophobic (oil) phase; and (3) a surfactant system.

The surfactant system of the water-in-oil emulsion comprises surfactants such as oil-soluble alkanolamides, polyoxyethylene derivatives of sorbitan esters, sorbitan monooleate, sorbitan monostearate, $C_6$–$C_{22}$ linear or branched alkyl ethoxylate with 1 to 30 oxyethylene units, $C_6$–$C_{22}$ linear or branched alkyl propoxylate with 1 to 30 oxypropylene units, $C_6$–$C_{22}$ linear or branched alkyl ethoxylate/propoxylate with 1 to 30 combined oxyethylene and propoxylate units, hexadecyl sodium pthalate, cetyl or stearyl sodium pthalate, ethylene oxide condensates of fatty acid amides. The preferred surfactant system comprises oil-soluble alkanolamides, polyoxyethylene derivatives of sorbitan esters, sorbitan monooleate, sorbitan monostearate, $C_8$–$C_{22}$ linear or branched alkyl ethoxylate with 1 to 25 oxyethylene units, $C_8$–$C_{22}$ linear or branched alkyl propoxylate with 1 to 25 oxypropylene units, $C_8$–$C_{22}$ linear or branched alkyl ethoxylate/propoxylate with 1 to 25 combined oxyethylene and propoxylate units. The most preferred surfactant system comprises oil-soluble alkanolamides, polyoxyethylene derivatives of sorbitan esters, sorbitan monooleate, sorbitan monostearate, $C_8$–$C_{18}$ linear or branched alkyl ethoxylate with 1 to 20 oxyethylene units, $C_8$–$C_{18}$ linear or branched alkyl propoxylate with 1 to 20 oxypropylene units, $C_8$–$C_{18}$ linear or branched alkyl ethoxylate/propoxylate with 1 to 20 combined oxyethylene and propoxylate units.

The hydrophobic oil phase of the water-in-oil emulsion comprises one or more natural, modified or synthetic oils such as mineral oil, available commercially as Blandol® from Witco, Drakeol® from Penreco or MagieSol® from Magie Bros. for example, Synthetic oils such as Isopar® and Exxate® from Exxon Chemical Company, and vegetable oils such as canola oil, coconut oil, rapeseed oil and the like.

The preferred hydrophobic oil phase comprises mineral oil, available commercially as Blandol® from Witco, Drakeol® from Penreco or MagieSol® from Magie Bros. for example, Synthetic oils such as Isopar® and Exxate® from Exxon Chemical Company.

The most preferred hydrophobic oil phase comprises mineral oil, available commercially as Blandol® from Witco, Drakeol® from Penreco, Synthetic oil such as Isopar® from Exxon Chemical Company The aqueous phase of the water-in-oil emulsion of this embodiment of the present invention comprises an amount of water and a polymer, the monomers in the polymer comprising: (a) 1 to about 100 mol % acrylamidopropyl-trimethyl ammonium chloride (APTAC), methacrylamidopropyltrimethyl ammonium chloride (MAPTAC), methyloyloxyethyl trimethyl ammonium chloride (METAC) methyloyloxyethyl trimethyl ammonium methylsulfate (METAMS), acryloyloxyethyl trimethyl ammonium chloride (AETAC) and/or dimethyl diallyl ammonium chloride (DMDAAC); (b) 0 to about 80 mol % acrylic acid (AA), methacrylic acid (MAA), 2-acrylamido-2-methylpropane sulfonic acid (AMPSA) and/or 2-methacrylamido-2-methylpropane sulfonic acid (MAMPSA); (c) 0 to about 1 mol % N,N'-methylenebisacrylamide (MBA), triallyl methyl ammonium chloride (TAMAC), allyl methacrylate (AM), n-methylol acrylamide (nMA), polyethylene glycol dimethacrylate (PEGDMA), ethylene glycol dimethacrylate (EGDMA), diethylene glycol dimethacrylate (DEGDMA), 1,6-hexanediol dimethacrylate (HDMA), and allyl sucrose (AS) and (d) 0 to about 70 mol percent, of a nonionic monomer selected from $C_1$–$C_3$ alkyl acrylate, $C_1$–$C_3$ alkyl methacrylate, acrylamide, n-alkyl acrylamide, methacrylamide, n-alkylmethacrylamide and/or diacetone acrylamide, wherein the upper mol percent of d) in the instant polymers is limited by emulsion stability considerations. Preferably, the mol ratio of a):b ranges from about 20:80 to about 95:5, more preferably from about 25:75 to about 75:25. Further, the weight average molecular weight of the polymer generated after the addition of a free radical initiator source, as determined by viscometry, is at least about 10,000, preferably from about 50,000 to about 10,000,000, more preferably from about 100,000 to about 8,000,000. Alternatively, gel permeation chromatography (GPC) with light scattering detection can be used.

Preferably, for the emulsion polymer the mol ratio of a):b) ranges from 25:75 to about 75:25, the preferred polymers contain 0 to 0.1 mol % of branching or crosslinking agent c), and the preferred polymers contain at least about 1 up to about 50 mol % of nonionic monomer (d) $C_1$–$C_3$ alkyl acrylate or $C_1$–$C_3$ alkyl methacrylate esters, acrylamide or methacrylamide. More preferably, the instant polymers contain about 5 to about 30 mol % of the acrylate or methacrylate ester, acrylamide or methacrylamide moiety. In the most preferred case, the nonionic monomer is methyl acrylate, methyl methacrylate, acrylamide or methacrylamide.

The aqueous phase of the water-in-oil emulsion polymer may alternatively comprise:
a) about 20 to about 95 mol % APTAC, MAPTAC, METAC, METAMS, AETAC or DMDAAC, preferably MAPTAC or DMDAAC;
b) about 5 to about 80 mol % acrylic acid, methacrylic acid, AMPSA or MAMPSA, preferably acrylic acid;
c) about 0 to about 0.1 mol % MBA, TAMAC, AM, nMA, PEGDMA, EGDMA, DEGDMA, HDMA or AS, preferably MBA, TAMAC or AS, and
d) 0.1 to about 50 mol %, preferably 1 to about 50 mol %, of a $C_1$–$C_3$ alkyl acrylate, $C_1$–$C_3$ alkyl methacrylate, acrylamide, n-alkyl acrylamide, methacrylamide, n-alkylmethacrylamide and/or diacetone acrylamide, preferably methyl acrylate, methyl methacrylate, acrylamide and methacrylamide and most methyl acrylate and acrylamide, wherein the molecular weight of said polymers is at least about 10,000.

The hydrophobic oil phase of the water-in-oil emulsion will comprise 10 to 60% by weight of the composition, preferably 15 to 50%, most preferably 17 to 35% by weight of the water-in oil emulsion polymer composition.

The surfactant system will comprise 0.5 to 10% by weight of the composition, preferably 1 to 7%, most preferably 1 to 5% by weight of the water-in-oil emulsion polymer composition.

The aqueous phase of the water-in-oil emulsion will comprise 5 to 90% by weight of the composition, preferably 10 to 80%, most preferably 30 to 80% by weight of the water-in-oil emulsion polymer composition.

Further, the instant invention is directed to a method for treating a substrate comprising contacting said substrate with the above defined water-in-oil emulsion polymer, preferably with an effective amount of said polymer or, an effective amount of an acceptable medium comprising from about 0.01 to about 20%, preferably from about 0.1 to about 10%, by weight, based on the total weight of said medium, of an instant water-in-oil polymer.

As used herein, the term "branched" refers to an addition polymer, made using a free radical initiator source, which has included in the mixture of monomers employed, some content of monomer that contains multiple polymerizable double bonds. Typically, these monomers will contain between two and six polymerizable double bonds. The resulting "branched" polymers can remain completely water soluble, water dispersible, or in the extreme be only water swellable. The latter is an example of crosslinking resulting from the situation in which the level of multi double bond containing monomer results in a crosslinked and or network structure which is well known to those skilled in the art of polymer synthesis.

As used herein, the term "active basis" refers to a concentration of additive based on the active solids in the stock solution.

As used herein, the term "effective amount" refers to that amount of a composition necessary to bring about a desired result, such as, for example, the amount needed to treat a keratin-containing substrate relative to a particular purpose, such as conditioning or the amount of a composition necessary to provide good ink jet printing on paper, such as minimal feathering.

Turning now to each of the components of the instant ampholyte polymers, the cationic component is either acrylamidopropyl-trimethyl ammonium chloride (APTAC) or methacrylamidopropyltrimethyl ammonium chloride (MAPTAC), which may be represented as follows:

MAPTAC

counter ion, preferably a halogen such as Cl⁻
APTAC

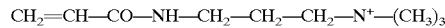

counter ion, preferably a halogen such as Cl⁻
METAC/METAMS

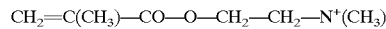

counter ion, preferably methylsulfate (METAMS), chloride (METAC) or other halogen
AETAC

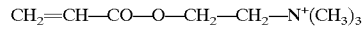

counter ion chloride or other halogen
DMDAAC

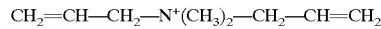

counter ion chloride or other halogen

These monomers are hydrolytically stable, which enable them to remain intact and interact with target substrates under severe temperature and pH conditions. MAPTAC is the preferred cationic monomer.

The cationic MAPTAC/APTAC monomer portion of the ampholyte polymers of the instant invention is present in an amount such that the cationic:anionic mol ratio ranges from about 20:80 to about 95:5

The second component of the ampholyte polymers of the present invention is the anionic monomer acrylic acid (AA) or methacrylic acid (MAA), which may be represented by the following formula:

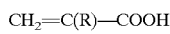

$CH_2=C(R)—COOH$ where R is H or $CH_3$.

Additionally, 2-acrylamido-2-methylpropane sulfonic acid (AMPSA) or 2-methacrylamido-2-methylpropane sulfonic acid (MAMPSA), preferably AMPSA, can be used as component (b), alone or in combination with acrylic acid or methacrylic acid. These monomers are represented as follows:

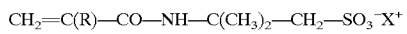

$CH_2=C(R)—CO—NH—C(CH_3)_2—CH_2—SO_3^-X^+$ wherein R=H or $CH_3$ and X=suitable salt forming cation.

The third component is the branching agent N,N'-methylenebisacrylamide (MBA), triallyl methyl ammonium chloride (TAMAC), allyl methacrylate (AM), n-methylol acrylamide (nMA), polyethylene glycol dimethacrylate (PEGDMA), ethylene glycol dimethacrylate (EGDMA), diethylene glycol dimethacrylate (DEGDMA), 1,6-hexanediol dimethacrylate (HDMA), or allyl sucrose (AS). The branching agent can be represented as follows:

$R_{2-6}—O$

Wherein R=acrylamide, methacrylamide, acrylate, methacrylate or allyl and
O=a glycol, polyol, sugar or $C_{1-12}$ alkane.

The fourth mer unit of the instant invention is an alkyl acrylate, methacrylate represented as follows:

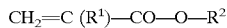

$CH_2=C(R^1)—CO—O—R^2$ wherein $R^1$=H or $CH_3$ and $R^2=C_1-C_3$
Acrylamide

$CH_2=CH—CO—NH_2$

Methacrylamide $CH_2=C(CH_3)—CO—NH_2$ n-Alkyl Acrylamide

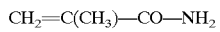

$CH_2=CH—CO—NHR$

R=$C_1-C_{22}$ linear or branched alkyl
n-AlkylMethacrylamide

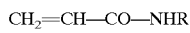

$CH_2=C(CH_3)—CO—NHR$

R=$C_1-C_{22}$ linear or branched alkyl
Diacetone Acrylamide

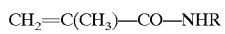

$CH_2=CH—CO—NH—C(CH_3)_2—CH_2—CO—CH_3$

The instant polymers may be prepared by conventional solution polymerization techniques, as indicated below and in the Examples. Thus, to prepare the instant polymers the appropriate weights for the desired mol %'s of DMDAAC/APTAC/MAPTAC, acrylic acid or other anionic monomers and MBA or other branching agent are charged to a glass reactor equipped with a stirring means. The desired amount of alkyl acrylate, methacrylate or acrylamide is then added to the reactor with vigorous stirring to give the desired total monomer concentration, which is generally about 10–25% by weight. The monomer mixture may then be adjusted to a pH of about 3.0 to about 6.5 with dilute NaOH, heated to about 55° C., and purged with nitrogen for at least thirty minutes. Polymerization is then initiated by adding about $5 \times 10^{-2}$ mol % of sodium persulfate and about $2.4 \times 10^{-3}$ mol % of sodium bisulfate. After the peak exotherm is reached, additional dilution water and sodium bisulfite are added to scavenge any residual monomer and to dilute the final product to 4–8% polymer solids.

The molecular weight of the ampholyte polymers of the present invention may be within the broad range of greater than about 10,000, preferably from about 50 thousand to about 10 million, and more preferably from about 100,000 to 8 million.

Reduced viscosity (dl/g) may be used as an approximate measure of the weight average molecular weight of the ampholyte polymers of the present invention. The values shown herein represent a capillary viscosity measured with Ubbelhhde Capillary Viscometer at 0.05% concentration of polymer in a 1M NaCl solution, pH 7, at 30° C. The resulting molecular weight value is calculated in accordance with methods well known in the art.

Cosmetically Acceptable Media

The water soluble polymers of the present invention are used as compositions for treating hair, skin and nails by incorporating them in a cosmetically acceptable medium in amounts of from 0.1–10% by weight of said terpolymer, and preferably in an amount of from 0.5 to 5% by weight of said water soluble polymer.

These compositions can be presented in various forms, i.e., various cosmetically acceptable media, such as a liquid, cream, emulsion, gel, thickening lotion or powder; they can contain water and also any cosmetically acceptable solvent, in particular monoalcohols, such as alkanols having 1 to 8 carbon atoms, like ethanol, isopropanol, benzyl alcohol and phenylethyl alcohol, polyalcohols, such as alkylene glycols, like glycerins, ethylene glycol and propylene glycol, and glycol ethers, such as mono-, di- and tri-ethylene glycol monoalkyl ethers, for example ethylene glycol monomethyl ether, ethylene glycol monomethyl ether and diethylene glycol monomethyl ether, used singly or in a mixture. These solvents can be present in proportions of up to as much as 70% by weight, relative to the weight of the total composition.

These compositions can also be packaged as an aerosol, in which case they can be applied either in the form of an aerosol spray or in the form of an aerosol foam.

As the propellant gas for these aerosols, it is possible to use, in particular, dimethyl ether, carbon dioxide, nitrogen, nitrous oxide and volatile hydrocarbons, such as butane, isobutane, propane and, possibly, chlorinated and fluorinated hydrocarbons, although the latter are falling into increasing environmental disfavor.

Preferred compositions can also contain electrolytes, such as aluminum chlorhydrate, alkali metal salts, e.g., sodium, potassium or lithium salts, these salts preferably being halides, such as the chloride or bromide, and the sulphate, or salts with organic acids, such as the acetates or lactates, and also alkaline earth metal salts, preferably the carbonates, silicates, nitrates, acetates, gluconates, pantothenates and lactates of calcium, magnesium and strontium.

These compositions can also be presented in the form of a powder or of lyophilisates to be diluted before use.

The compositions according to the present invention can contain any other ingredient normally used in cosmetics, such as perfumes, dyestuffs which can serve to color the composition itself or the fibres of the hair, preservatives, sequestering agents, thickeners, silicones, softeners, foam synergistic agents, foam stabilisers, sun filters, peptising agents and also anionic, non-ionic, cationic or amphoteric surface-active agents or mixtures thereof.

These compositions can be used, in particular, in the form of a shampoo, a rinsing lotion, a cream or a treatment product which can be applied before or after coloring or bleaching, before or after shampooing, before or after perming or before or after straightening, and can also adopt the form of a coloring product, a setting lotion, a brushing lotion, a bleaching product, a perming product or a straightening product.

A particularly preferred embodiment consists of use in the form of a shampoo for washing the hair.

In this case, these compositions contain anionic, cationic, nonionic or amphoteric surface-active agents typically in an amount from 3 to 50% by weight, preferably 3 to 20%, and their pH is 3 to 10, preferably 4 to 9 and most preferably 4.5 to 8.5.

A list of the surface-active agents which can be used according to the invention is given in U.S. Pat. Nos. 4,240,450; 4,445,521; and 4,719,099.

Another preferred embodiment consists of use in the form of a rinsing lotion to be applied mainly before or after shampooings. These lotions are typically aqueous or aqueous-alcoholic solutions, emulsions, thickened lotions or gels. If the compositions are presented in the form of an emulsion, they can be nonionic, anionic or cationic. The nonionic emulsions consist mainly of a mixture of an oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially carbopol, xanthan gums, sodium alginates, gum arabic and cellulose derivatives, and it is also possible to achieve thickening by means of a mixture of polyethylene glycol stearate or distearate or by means of a mixture of a phosphoric acid ester and an amide. The concentration of thickener is suitably 0.05 to 15% by weight. If the compositions are presented in the form of a styling lotion, shaping lotion or setting lotion, they generally comprise, in aqueous, alcoholic or aqueous-alcoholic solution, the ampholyte tezpolymers defined above.

If the compositions of the invention are intended for use in the dyeing of keratin fibres, and in particular human hair, they contain at least one oxidation dyestuff precursor and/or one direct dyestuff, in addition to the ampholyte terpolymer. They can also contain any other adjuvant normally used in this type of composition.

The pH of the dyeing compositions is generally 7 to 11, and can be adjusted to the desired value by adding an alkalizing agent.

The composition according to the present invention can also be used for waving or straightening the hair. In this case, the composition contains, in addition to the ampholyte terpolymer, one or more reducing agents and, if appropriate, other adjuvants normally used in this type of composition; such compositions are intended for use conjointly with a neutralizing composition. The composition according to the present invention can also be used for skin care products such as those that are primarily "leave on" formulations such as moisturizing lotions, emulsions and creams and sunscreen formulations. Other skin care products would include "rinse off" formulations such as bar soaps, liquid hand soaps, disinfecting soaps and shower gels. These "rinse off" formulations can be comprised of a variety of surfactants as outlined above, alkali salts of fatty acids (soaps) or combinations of each.

The composition of the instant invention can generally be successfully added to aqueous cellulosic furnishes over the entire pH range customarily employed in the papermaking process. Preferably, the composition of the instant invention is added to aqueous cellulosic furnishes having a pH from about 3 to 10. Therefore, it will be appreciated by those skilled in the art that the composition of the instant invention may be added to aqueous cellulosic paper furnishes that are acid, alkaline, or neutral in character. It will be understood by those skilled in the art that generally an acid furnish has a pH range from about 3.0 to 5.5, an alkaline furnish has a pH range from about 7.0 to greater than about 10.0, and a neutral furnish has a pH range of from about 5.5 to 7.0.

In another embodiment of this invention, a process is provided for in which paper or paperboard having improved properties is made by forming an aqueous cellulosic paper furnish which comprises adding to the furnish an effective amount, based on the dry weight of the solids of the furnish, of a high molecular weight branched ampholytic polymer, as hereinbefore described.

The instant invention is also directed to a method for drilling a well in a subterranean formation comprising circulating into the well, during drilling an aqueous drilling fluid, the improvement wherein said aqueous drilling fluid comprises:

(a) an aqueous clay dispersion; and
(b) the above-described polymer.

The clay dispersion may be any finely divided solid which is capable of being dispersed or suspended in an aqueous liquid vehicle. Ordinarily, such material will include hydratable clay or colloidal clay bodies such as Wyoming bentonite, commercial medium-yield drilling clays mined in various parts of the country such as in Texas, Tennessee and Louisiana, and those produced when clay subsurface formations are drilled. Weighting materials added to increase specific gravity such as barites, iron oxide, and the like may also be included.

The aqueous medium may be fresh water such as is obtained from wells or streams; it may be salt water from the sea or from wells; or, it may even include oil-in-water emulsions, i.e., water which has become contaminated in some way with small quantities of oil, or to which such oil has been added to gain some desired advantage. The polymers of the instant invention were found to be particularly effective in salt water and to be stable at high temperature. The drilling mud containing the polymers of the instant invention show both good filtration and rheology properties.

It is contemplated that the drilling muds of the invention may also contain other additives besides the polymers of the invention. Materials such as caustic, quebracho, lime and the like may be added to the drilling mud at the surface while other materials such as gypsum, shale and the like may be encountered in subsurface formations during drilling operations.

When employed in accordance with the invention, the polymer may be added directly to the drilling mud as a dry powder, as a slurry suspended in a suitable liquid, or as a solution in water or some other suitable solvent, and they may be incorporated therein at any convenient point in the mud circulation system. It may be desirable to employ a mixing device such as a cone and jet mixer or the equivalent for incorporating the additive in the mud.

The present invention is also directed to cementing compositions that are useful in oil, gas and water well cementing operations since such compositions have reduced fluid loss to the surrounding formation. Such compositions are used to cement a conduit penetrating a permeable earthen formation via introducing such composition into the space between such conduit and such formation and allowing the composition to harden. These cementing compositions for use in oil, gas and water well cementing operations comprise water, hydraulic cement, and the branched ampholyte polymer of the present invention.

EXAMPLES

Example 1

Preparation of a 50/26/24 M/M Water-In-Oil Emulsion Polymer of Am/Dmdaac/Aa

A 50/26/24 M/M/M/M polymer of acrylamide/DMDAAC/acrylic acid was prepared as follows:

1. Zeolite softened water, 49% aqueous acrylamide solution, 65% aqueous DMDAAC solution and acrylic acid and 50% sodium hydroxide (Items 1, 2, 3, 4 and 5 in Table 1, below) were added to a glass beaker in the amounts shown, and stirred until uniform.
2. Mineral oil (Draketex® 50 from Penreco), a diethanolamide of tall oil fatty acid, polyoxyethylene (5) sorbitan monooleate and an oil soluble free radical initiator, azo-bis-isobutyronitrile (AIBN) (Items 6,7,8 and 9 in Table 1, below) were added to a separate glass beaker in the amounts shown, and stirred until uniform.
2. The mixture from (2) was added to a glass resin kettle and once agitation was begun, the mixture from (1) was added to the resin kettle. The resulting emulsion was sparged with nitrogen for 30 minutes ahile the temperature equilibrated to 30° C.
3. 75 microliters of t-butyl hydroperoxide were added to the stirring emulsion and 0.075% sodium metabisulfite solution was fed at 0.1 milliliters per minute.
4. After 75 minutes, the temperature rose from 30° C. to 100° C. at which point the emulsion was cooled to room temperature.

The resulting water-in-oil emulsion polymer, which represents the best mode known to the inventors, had a reduced viscosity measured at 0.1% in 1N NaCl at 30° C. of 8.9 dl/g.

TABLE 1

Am/DMDAAC/AA water-in-oil emulsion polymer 50/26/24 m/m/m

| ITEM | NAME | WEIGHT % |
|---|---|---|
| 1 | Zeolite Softened Water | 18.237 |
| 2 | Acrylamide, 49% active | 24.277 |
| 3 | DMDAAC, 65% active | 21.541 |
| 4 | Acrylic Acid, 100% active | 5.319 |
| 5 | Sodium Hydroxide, 50% active | 5.667 |
| 6 | Mineral Oil | 22.598 |
| 7 | Diethanolamide of tall oil fatty acid, 100% | 1.564 |

TABLE 1-continued

Am/DMDAAC/AA water-in-oil emulsion polymer 50/26/24 m/m/m

| ITEM | NAME | WEIGHT % |
|---|---|---|
| 10 | active polyoxyethylene (5) sorbitan monooleate 100% active | 0.521 |
| 12 | AIBN, 100% active | 0.014 |
| 13 | t-butyl hydroperoxide, 100% active | 0.001 |
| 14 | Sodium metabisulfite, 0.075% acive | 0.261 |

This sample had a Brookfield Viscosity (LV, spindle #2, @6 rpm, 25° C.)=4,100 cps.

Example 2

The polymer of Example 1 (50/26/24 m/m/m Am/DMDAAC/AA) was tested in a typical Shampoo. This polymer was tested for wet comb versus a control, MERQUAT® Plus 3331, a solution polymer of the same composition as the water-in-oil emulsion polymer of Example 1 sold by Calgon Corporation.

TABLE 2

| | Wet Comb Total Work (mJ) | |
|---|---|---|
| | Am/DMDAAC/AA | MERQUAT® Plus 3331 |
| Shampoo #1 | 53.2 | 164.8 |

The water-in-oil emulsion polymer of example 1 performed surprisingly better than the comparative commercial sample of the same composition.

Example 3

An aqueous clay based drilling mud is prepared using the polymer of Example 1 (50/26/24 m/m/m Am/DMDAAC/AA) as outlined in Table 3.

TABLE 3

Clay Based Gypsum Drilling Mud

| Ingredient | Percent (w/w %) |
|---|---|
| Water | 86.0 |
| Bentonite | 3.5 |
| Rev Dust | 7.5 |
| Gypsum | 1.0 |
| Lignonsulfate | 1.0 |
| Polymer of Example 1 | 0.5 |
| Caustic | 0.5 |

The clay based gypsum drilling mud is aged for 16 hours at 325° F. and then cooled. The resulting API filtrate reading is lower for the formula of the example when compared to a corresponding clay based gypsum drilling mud without polymer.

Example 4

A cementing composition is prepared using the polymer of Example 1 (50/26/24 m/m/m Am/DMDAAC/AA) as outlined in Table 4.

TABLE 4

| Cemeting Composition | |
| --- | --- |
| Ingredient | Percent (w/w %) |
| Water | 46.0 |
| Class H Cement | 43.0 |
| Polymer of Example 1 | 1.0 |

The cementing composition is mixed into a slurry. The resulting API filtrate reading (30 minute, 125° F., 1,000 psi) is lower for the formula of the example when compared to a corresponding cementing composition without polymer.

What is claimed is:

1. A method for treating hair, skin or nails comprising contacting the hair, skin or nails with a composition comprising 0.1% to 10% by weight, in a cosmetically acceptable medium, of a branched or crosslinked ampholyte polymer comprising:

a.) about 20 to about 95 mol % acrylamidopropyltrimethyl ammonium halide, methacrylamidopropyltrimethyl ammonium halide, methyloyloxyethyl trimethyl ammonium halide, methyloyloxyethyl trimethyl ammonium methylsulfates, acryloyloxyethyl trimethylammonium halide or dimethyl diallyl ammonium halide;

b.) about 5 to about 80 mol % of acrylic acid, methacrylic acid, 2-acrylamido-2-methylpropane sulfonic acid or 2-methacrylamido-2-methylpropane sulfonic acid;

c.) about 0.0001 to about 1 mol % N,N'-metyhylenebisacrylamide triallyl methyl ammonium chloride, allyl methacrylate, N-methylol acrylamide, polyethylene glycol dimethacrylate, ethylene glycol dimethacrylate, ethylene glycol dimethacrylate, diethylene glycol dimethacrylate, 1,6-hexanediol dimethacrylate, and allyl sucrose; and d.) about 1 to about 50 mol % of $C_1$–$C_3$ alkyl methacrylate, $C_1$–$C_3$ alkyl acrylate, acrylamide, N-alkylacrylamide, methacrylamide, N-alkylmethacrylamide, and diacetone acrylamide; wherein the weight average molecular weight of said polymer, as determined by viscometry, is at least about 10,000.

2. A composition for treating hair, skin and nails which comprises 0.1% to 10% by weight in a cosmetically acceptable medium of a branched or crosslinked ampholyte polymer comprising:

a.) about 20 to about 95 mol % acrylamidopropyltrimethyl ammonium halide, methacrylamidopropyltrimethyl ammonium halide, methyloyloxyethyl trimethyl ammonium halide, methyloyloxyethyl trimethyl ammonium methylsulfates, acryloyloxyethyl trimethylammonium halide or dimethyl diallyl ammonium halide;

b.) about 5 to about 80 mol % of acrylic acid, methacrylic acid, 2-acrylamido-2-methylpropane sulfonic acid or 2-methacrylamido-2-methylpropane sulfonic acid;

c.) about 0.0001 to about 1 mol % N,N'-metyhylenebisacrylamide, triallyl methyl ammonium chloride, allyl methacrylate, N-methylol acrylamide, polyethylene glycol dimethacrylate, ethylene glycol dimethacrylate, ethylene glycol dimethacrylate, diethylene glycol dimethacrylate, 1,6-hexanediol dimethacrylate, and allyl sucrose; and d.) about 1 to about 50 mol % of $C_1$–$C_3$ alkyl methacrylate, $C_1$–$C_3$ alkyl acrylate, acrylamide, N-alkylacrylamide, methacrylamide, N-alkylmethacrylamide, and diacetone acrylamide; wherein the weight average molecular weight of said polymer, as determined by viscometry, is at least about 10,000.

3. The method of claim 1, wherein a) is methacrylamidopropyltrimethyl ammonium chloride, b) is acrylic acid, c) is N,N'-methylenebisacryamide, and d) is methyl acrylate.

4. The method of claim 1, wherein said molecular weight ranges from about 50,000 to about 10,000,000.

5. The method of claim 1 wherein the branched or crosslinked ampholyte polymer comprises:

a) about 25 to about 75 mol % acrylamidopropyltrimethyl ammonium chloride, methacrylamidopropyltrimethyl ammonium chloride, or dimethyldiallylammonium chloride;

b) about 25 to about 75 mol % acrylic acid or methacrylic acid;

c) about 0.0001 to 0.1 mol % N,N'-methylenebisacrylamide triallyl methyl ammonium chloride or allyl sucrose; and d) about 1 to about 35 mol % of a $C_1$–$C_3$ alkyl acrylate, $C_1$–$C_3$ alkyl methacrylate, acrylamide, N-alkyl acrylamide, methacrylamide, N-alkyl methacrylamide or diacetone acrylamide wherein the molecular weight of said polymer is at least about 10,000.

* * * * *

UNITED STATES PATENT AND TRADEMARK OFFICE
CERTIFICATE OF CORRECTION

PATENT NO. : 6,691,715 B2
DATED : February 17, 2004
INVENTOR(S) : Matz et al.

It is certified that error appears in the above-identified patent and that said Letters Patent is hereby corrected as shown below:

Column 17,
Line 21, "and" should be -- or -- (first occurrence)

Column 18,
Line 21, "and" should be -- or -- (first occurrence)

Signed and Sealed this

Ninth Day of November, 2004

JON W. DUDAS
*Director of the United States Patent and Trademark Office*